United States Patent [19]

Johnsen et al.

[11] Patent Number: 5,340,550
[45] Date of Patent: Aug. 23, 1994

[54] INSTRUMENT STERILIZATION CONTAINER

[75] Inventors: James B. Johnsen; Hal J. Oien, both of Beaverton, Oreg.

[73] Assignee: Jordco, Inc., Beaverton, Oreg.

[21] Appl. No.: 969,974

[22] Filed: Nov. 2, 1992

[51] Int. Cl.⁵ .................. A61L 2/00; A61B 19/02; B65D 21/02
[52] U.S. Cl. .................. 422/292; 422/102; 206/438; 206/509; 220/23.83; 220/367; 220/DIG. 27
[58] Field of Search ............ 206/363, 370, 438, 509; 220/23.83, DIG. 27, 367; 422/102, 292

[56] References Cited

U.S. PATENT DOCUMENTS

| 2,340,024 | 1/1944 | Skaller | 220/367 X |
|---|---|---|---|
| 3,530,979 | 9/1970 | Merrill, Jr. et al. | 206/438 X |
| 3,579,306 | 5/1971 | Crane | 206/438 X |
| 3,696,916 | 10/1972 | Penniman et al. | 206/16.6 |
| 3,783,996 | 1/1974 | Gerard et al. | 206/17.5 |
| 3,881,868 | 5/1975 | Duke | 206/63.5 X |
| 4,251,482 | 2/1981 | Sanderson et al. | 422/26 |
| 4,402,407 | 9/1983 | Maly | 206/438 |
| 4,512,471 | 4/1985 | Kaster et al. | 206/438 |
| 4,609,126 | 9/1986 | Janda | 220/367 X |
| 4,706,839 | 11/1987 | Spence | 206/438 X |
| 4,762,247 | 8/1988 | Temmesfeld | 220/367 X |
| 4,859,423 | 8/1989 | Perlman | 422/102 |
| 4,867,305 | 9/1989 | Schneider | 206/368 X |
| 4,960,220 | 10/1990 | Foa | 220/23.83 |
| 5,076,437 | 12/1991 | Schindler | 206/509 X |
| 5,156,290 | 10/1992 | Rodrigues | 220/367 X |

Primary Examiner—Lyle A. Alexander
Assistant Examiner—Milton I. Cano
Attorney, Agent, or Firm—Kolisch Hartwell Dickinson McCormack & Heuser

[57] ABSTRACT

A sterilization container is provided which includes interengageable, overlapping, hollow cap and base portions which, when combined, define a cavity and a fluid passage in the region of overlap to allow for continuous fluid flow from the outside to the inside of the container.

10 Claims, 2 Drawing Sheets

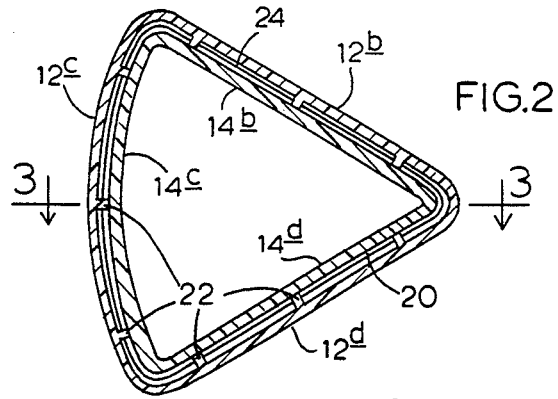
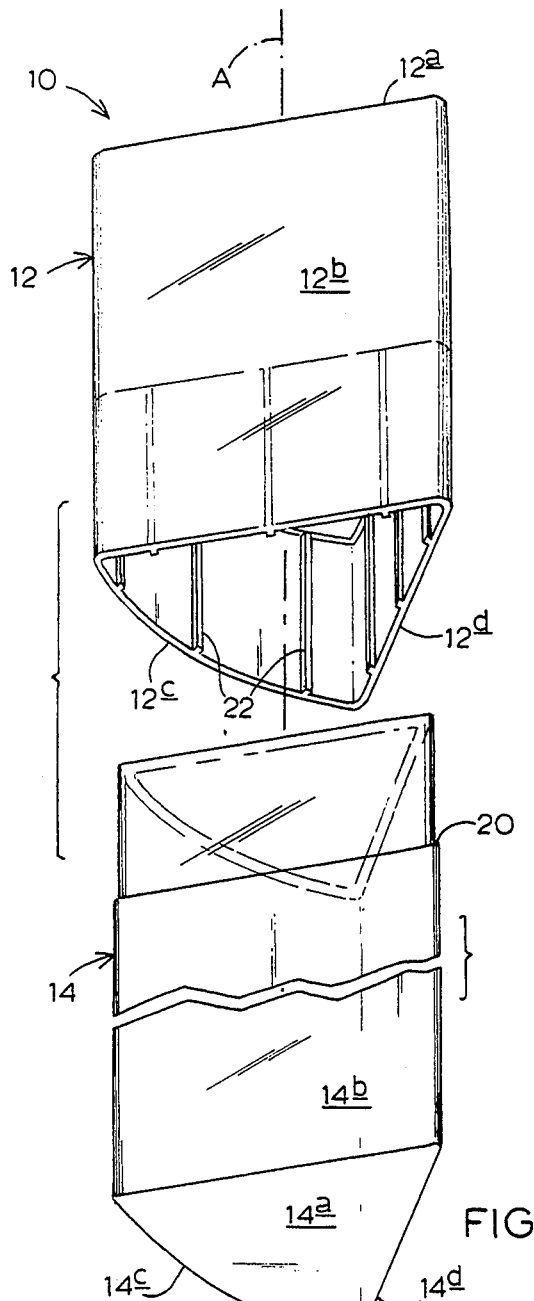
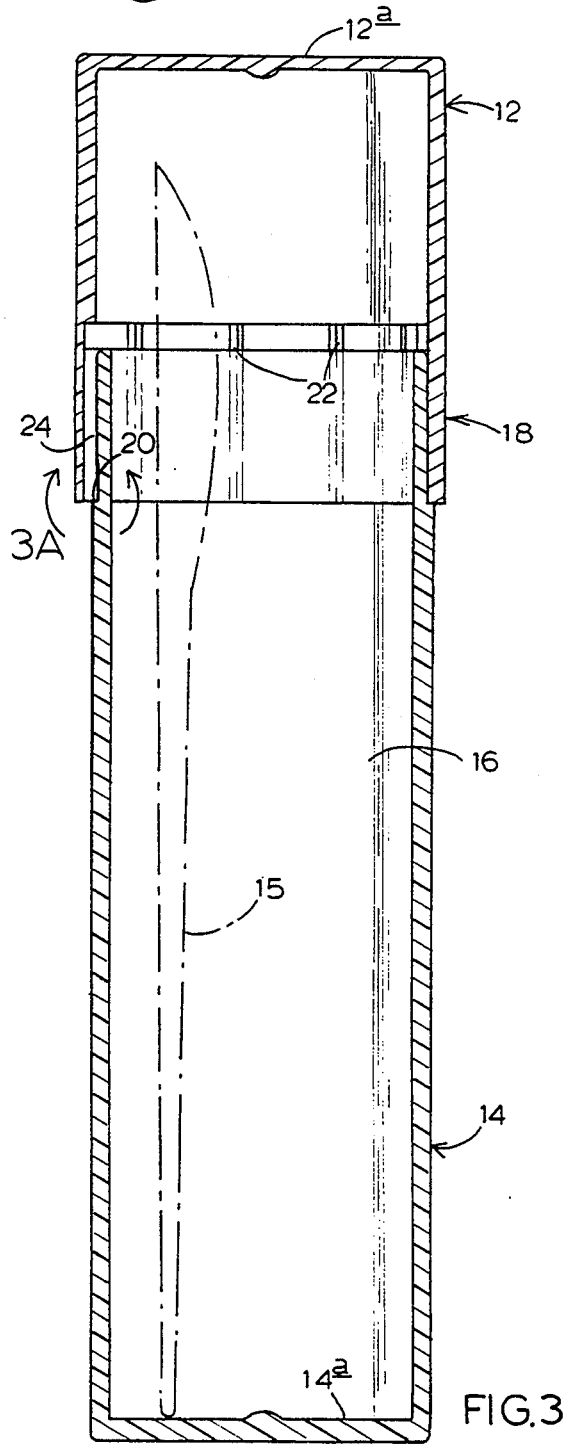
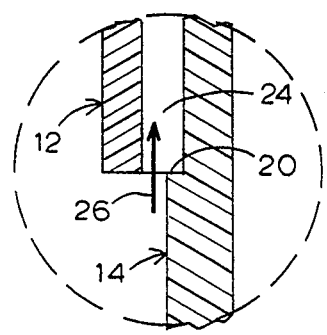

//\# INSTRUMENT STERILIZATION CONTAINER

BACKGROUND OF THE INVENTION

This invention relates generally to containers, and more particularly to a sterilization container which provides for the fail-safe passage of gas sterilant to the inside of the container without compromising safe containment of its contents. The invented container is useful in the sterilization of a variety of objects, but has proven especially useful in connection with the sterilization and storage of medical instruments and is described as such herein.

Sterilization of medical instruments has long been recognized as an effective way of preventing infection which may result from intrusive surgical procedures. Such infection may be caused by carriage of microorganisms or other contaminants into the body via surgical instruments during a surgical procedure. In an attempt to curb infection, instruments have typically been sterilized by placing them into a container and then placing the container into a sterilization autoclave. In the autoclave, the container and instruments are subjected to a sterilization medium which penetrates the container, sterilizing the instruments held therein. Once sterilization is completed, the container is removed from the autoclave and stored until the instruments are to be used.

Over the years, numerous containers have been developed for specific use in the sterilization and storage of medical instruments. Containers have been formed of metal, of plastic, of glass, and of paper, each of these materials being adaptable to define a sealed compartment once sterilization has been accomplished. Known containers, however, have been characterized by a variety of problems related to cost and functionality. Metal containers, for example, often include sterilizing gas inlet valves which are both complex and expensive. Such containers also are inadequate in that they do not allow for ready identification of instruments contained within the container once sterilized unless the sterilization seal is broken. Conventional plastic sterilization containers may allow identification, but known systems do not provide for passage of gas sterilant into the container while the lid is fitted thereto. When using plastic sterilization containers, instruments must therefore be sterilized without the lid in place, leading to the possibility of post-sterilization contamination or to operator injury due to the projection of sharp instruments beyond the confines of the container's base. Further, many prior art systems are actually highly perforated and allow readily for gas passage, but present the problem that once the sterilized package is removed from the sterilizing environment the perforations expose the just sterilized instrument to recontamination. Glass containers also allow view of their contents but are subject to easy breakage and have proven difficult to seal. Use of paper containers has similarly resulted in problems, such containers often being plagued by their susceptibility to puncture which may lead both to operator injury and to contamination of the instruments contained therein.

The above-cited disadvantages often necessitate repetitive sterilization and detract from the safety available to both sterilization equipment operators and to patients on whom the presumably sterilized instruments are used. A demand has therefore arisen for a sterilization container which provides for the safe containment of objects both during sterilization, and thereafter, without the necessity of the complex valve structures now in use.

Another issue arising in the sterilization of medical instruments concerns the efficiency with which the instruments can be sterilized, most known sterilization containers being designed with little or no consideration given to the size or shape of the autoclave in which sterilization is to occur. A conventional sterilizing autoclave, for example, includes a relatively small cylindrical chamber in which the instruments are to be placed for sterilization. Little has previously been done to accommodate the sterilization of instruments which have been placed in a container to maximize use of the limited autoclave space. Such inefficient use of space leads to wasted time and wasted resources due to repetitive autoclave operation. It is therefore an object of this invention to provide a sterilization container which maximizes the use of space within the chamber of an autoclave during the sterilization procedure.

SUMMARY OF THE INVENTION

Accordingly, a sterilization container is herein provided which includes interengageable, overlapping, hollow cap and base portions which, when fitted together, define a cavity and a fluid passage in the region of overlap to allow for continuous fluid flow from the exterior to the interior of the container. Fluid sterilant is thus allowed to flow through the passage and into the cavity to effect sterilization of instruments contained therein without the necessity of removing the cap.

In order to avoid contamination of instruments in the container once sterilization has been accomplished, the cap and base are formed so that the fluid passage defined by their combination provides a sterilant passage which requires flow of sterilant fluid into the container to pass in a direction generally parallel to the sides of the container. Particulate matter (microorganisms), which often is responsible for contamination of medical instruments, and which does not tend to pass in such a direction, is thus prevented from entering the container and a sterile environment is maintained.

In order to make better use of the space available in the sterilization autoclave, the invented sterilization container is shaped such that it may be combined with a variety of similar sterilization containers in a complementary manner to more efficiently utilize all of the space within the autoclave's sterilization chamber. Each container is thus designed to conform to a modular unit of space within the autoclave's sterilization chamber without significantly impeding the flow of sterilant into or out of that container or the containers adjacent thereto. Other features of the invented sterilization container will become apparent upon reference to the enclosed drawings and upon reading of the specification set forth below.

BRIEF DESCRIPTION OF THE DRAWINGS

FIG. 1 is an exploded perspective view of one embodiment of the invented sterilization container, such container including a cap and a base.

FIG. 2 is a sectional plan view of the container shown in FIG. 1, the section being taken through a region of cap/base overlap when the cap and base are combined.

FIG. 3 is a sectional view taken generally along the lines 3—3 of the container depicted in FIG. 2.

FIG. 3A is an enlarged fragmentary view of the area defined by 3A—3A in FIG.

DETAILED DESCRIPTION OF THE PREFERRED EMBODIMENT

Figure 4:
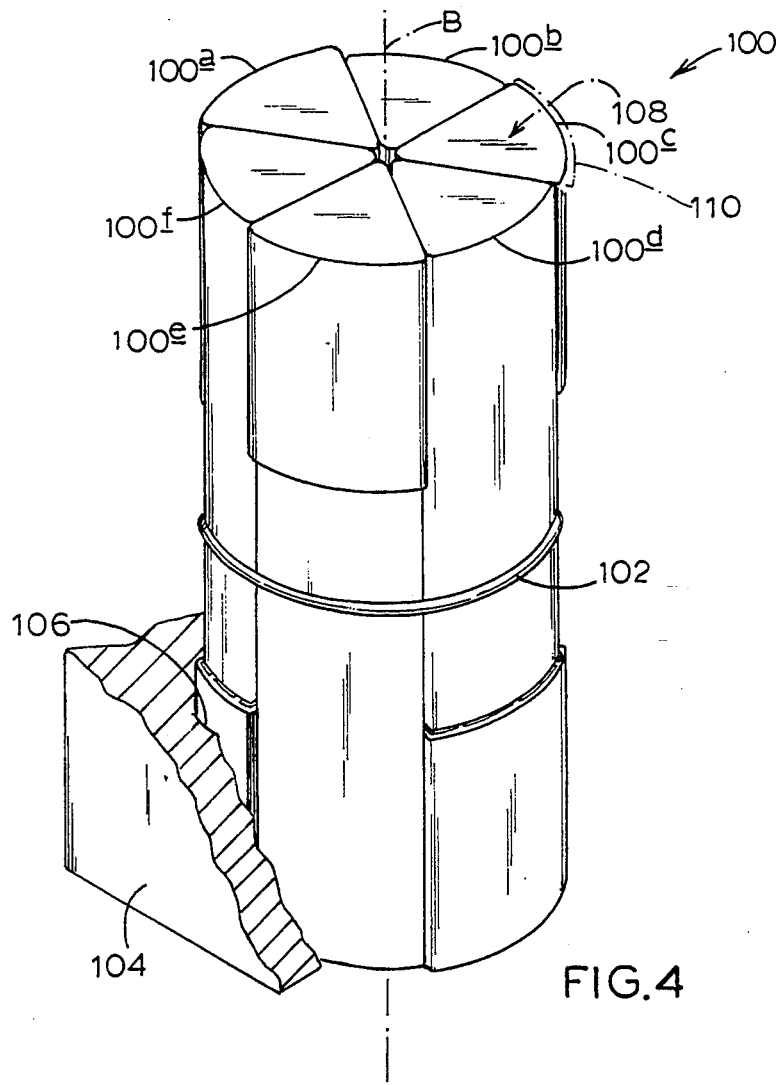
FIG. 4 is a perspective view of a cluster of sterilization containers similar to the container depicted in FIGS. 1-3, the containers forming a generally cylindrical sterilization system for placement in an autoclave shown in fragment.

As stated above, the present invention relates to a container for use in the sterilization and storage of objects, such container being particularly suited for the sterilization and storage of medical instruments. As will be described herein, the invented container is configured to maximize efficient use of available space while maintaining failsafe passage of gas sterilant to an object contained therein. A preferred embodiment of the invented container has been depicted in the drawings and is indicated generally at 10.

Beginning with a general overview of the invented container, and referring initially to FIGS. 1-3, the reader will see that container 10 includes, as its principle components, a cap 12 and a base 14. Both the cap and base take the form of elongate tubes, each having oppositely disposed open and closed ends. The two components, it will be appreciated, are of similar hollow cross-sectional shape and are suited for selected reversible combination along a longitudinal axis A.

When combined, the cap and base collectively define an elongate cavity 16 wherein objects such as medical instrument 15 may be safely sterilized and stored. As best shown in FIG. 3, the cavity is of a length longer than either the cap or base alone, an object held within the container thus being able to extend beyond the base's open end, even with the cap in place. Such an arrangement, it will be understood, allows for unobstructed gripping of the object when the cap is separated from the base. This feature is especially useful where the container holds sharp objects such as instrument 15. While instrument 15 is shown to have a length that permits it to extend above the top of the bases open end, a preferable base design for most applications will be one wherein the base is actually somewhat longer than the longest expected-too-be-handled instruments so that, under no circumstance, will an end of an instrument, such as a sharp end, project above the open top of the base.

Turning now to a particular description of cap 12, it will initially be noted that the cap is of pie-shaped cross-section giving the resultant container assembly a base/cap combined outer surface with a generally triangular configuration when viewed along axis A from above. The cap is rigid and fluid-impervious, preferably being formed from a material such as transparent plastic. The finished cap includes a top 12a, which defines the cap's closed end, and a plurality of sides 12b, 12c, 12d. The sides define a fluid-impervious surface structure which extends between the cap's open and closed ends. Referring to FIG. 2, it will be apparent that sides 12a and 12b are generally planar and that side 12c is arcuate about an axis parallel to axis A. As also shown in FIG. 2, the sides all intersect in arcuate corners for reasons which will be made clear below. Top 12a is also planar and includes rounded edges as indicated in FIG. 3.

Base 14 is also of generally pie-shaped cross-section, its open end being sized so as to fit into the open end of cap 12. Like the cap, the base is rigid and fluid-impervious and is formed from a material such as transparent plastic. The base thus includes a bottom 14a, which defines the base's closed end, and a plurality of sides 14b, 14c, 14d. The base's sides define a fluid-impervious surface structure which extends between the base's open and closed ends. Referring again to FIG. 2, the reader will note that the sides of base 14 substantially conform to the sides of cap 12, sides 14b and 14d, being generally planar and side 14c being arcuate about an axis parallel to axis A. As was the case with the cap, the base's sides intersect in rounded corners. The base's bottom also has rounded corners and is generally planar, providing a surface on which the container may stand.

Focusing attention now on the relationship between the cap and base, and referring specifically to FIG. 3, it will be noted that, upon combination of the cap and base, a region of longitudinal-surface-structure overlap 18 is defined along the container's length. The overlap region extends about the perimeter of the container, the cap and base being in direct contact with one another when the two are fittingly engaged. As mentioned above, region 18 is preferably of a length which is less than the length of either the cap or the base, the resulting cavity or inside of the container having a length greater than the length of either the cap or base. In the preferred embodiment, the base is approximately 7-inches long, the cap is approximately 3-inches long, and the region of overlap is approximately 1-inch long. The sides of the base and cap are approximately 2½-inches wide and on the order of 1/16-inch to ⅛-inch thick. Such proportions make for stable combination of the cap and base.

The sides of base 14 are recessed to a predetermined distance from the base's open end to define a ledge 20 which parametrically extends about the outside of the base. Such ledge, it will be noted, corresponds in position to the length of overlap region 18, the cap resting on the ledge when in place. The cap includes a plurality of perimetrally-spaced, elongate spines 22, each such spine extending longitudinally along the inside of the cap from adjacent the cap's open end to a predetermined distance therefrom. As indicated in FIG. 3, the length of the spines is preferably greater than the distance from the base's open end to ledge 20.

Referring still to FIG. 3, and bringing FIG. 3A into the discussion, it will be noted that the spines establish recessed channels in the cap, such channels serving, in concert with the base, to define sterilant fluid passages 24. Passages 24 provide for fluid communication between the outside and inside of the container when the cap is in place. Such communication is possible because the spines are of a thickness greater than the thickness of ledge 20. Openings thus exist in the area of the base's ledge, even with the cap in place. Additionally, because spines 22 extend into the cap a distance greater than the distance from the base's open end to ledge 20, the passages open internally to cavity 16. Fluid passages 24 are therefore non-closable upon simple combination of the cap and base.

As stated above, ledge 20 and spines 22 act in concert to limit overlapping passage of the cap over the base 14. Such limiting action is effected by direct engagement of the spines 22 against the ledge 20. The cap thus fits over the base only to the extent that the open end of the base is spaced from the ledge with the interior-most surfaces of the spines engaging the exterior-most surface of the base in the region of overlap. Such cooperative combination may be considered as an interengaged fitment means with spines 22 acting as cap fitment structure and ledge 20 acting as base fitment structure. The fitment structure, it will be understood, thus dictate a tight-fitting interengaging relationship between the cap and base.

By virtue of the nature of the fluid passages defined in the region of surface structure overlap between the cap and base, it will be appreciated that passage of sterilant fluid into the container is allowed only in a longitudinal direction which is toward the cap from the base as indicated by arrow 26 in FIG. 3A. Such limitation of fluid entrance serves to limit entrance of contaminants into cavity 16 while allowing entrance of sterilant fluid.

Turning now to a discussion of FIG. 4, the reader will appreciate that a sterilization system 100 may be created by combining containers in a cluster as shown. In such a system, each container is suitable for containment of an instrument or instrument set and the containers may be held together by a restraining member such as flexible band 102. In the embodiment of FIG. 4, it will be noted that the system is made up of plural containers 100a–f, each such container corresponding in cross-sectional shape to the container shown in FIGS. 1–3. The container cluster is selectively placed in a sterilization device such as autoclave 104, such cluster resting in an inner chamber 106 which extends along an insertion axis B. The inner chamber, it will be appreciated, may be considered to include one or more modular compartment 108, real or imaginary. As indicated, such compartments are defined in the inner chamber of a sterilization device by modular boundaries such as that shown by phantom lines 110 in FIG. 4. These boundaries may encompass one or more container, the surface structure of such containers being generally congruent therewith.

Figure 5:
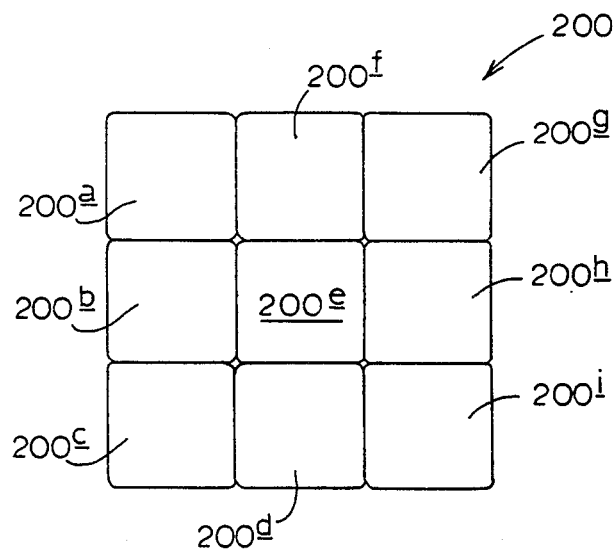
FIG. 5 is a highly simplified plan view of an alternative container cluster arrangement, each container being of a generally square cross-sectional shape.
Figure 6:
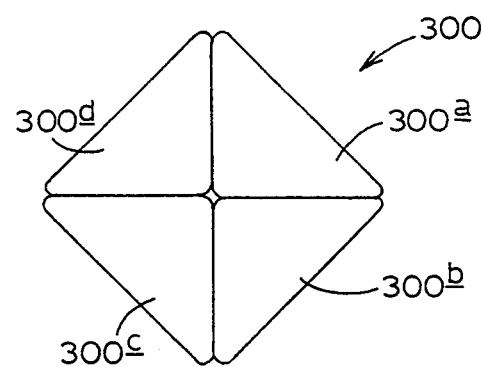
FIG. 6 is a highly simplified plan view of a second alternative container cluster arrangement, each container being of generally triangular cross-sectional shape.

Although in the modular system of FIG. 4, the cluster takes the form of a cylinder made up of pie-shaped containers, it should be appreciated that the containers could take various shapes. In FIG. 5, for example, a square container cluster 200 is represented, such cluster being formed from plural square containers 200a–i. In FIG. 6, a square cluster 300 is shown, such cluster being formed from four (4) triangular containers 300a–d.

As shown in FIG. 4, the containers are preferably alternated in longitudinal orientation, the cap of one container being adjacent the closed end of another container's base. In this manner, and by virtue of the rounded corners described above, fluid passage is made possible from the exterior to the interior of the container even where the container is surrounded by other containers in close proximity thereto.

Although a preferred embodiment of the invention has been disclosed, it should be appreciated that variations and modification may be made thereto without departing from the scope of the invention as defined by the appended claims.

It is claimed and desired to secure by Letters Patent:

1. A two-piece instrument sterilization container comprising an elongate, hollow base of generally triangular cross section, said base including fluid-impervious surface structure extending between an open end and a closed end in the base, and base fitment structure formed on said fluid-impervious surface structure adjacent said open end, and an elongate, hollow cap of generally triangular cross section, said cap including fluid-impervious surface structure extending between a closed end and an open end in the cap, and cap fitment structure formed on said fluid-impervious surface structure adjacent to said open end, said cap being removably fittable on and with respect to said base with the base and cap surface structures accommodating reversible, direct-contact, longitudinal-surface-structure fitment overlap between said base and cap, said fitment structures, with the base and cap fitted together, forming a non-closeable fluid passage in the region of overlap, which passage communicates between the outside and the inside of the container.

2. The container of claim 1, wherein said fluid passage is structured to allow fluid from outside the container enter the passage generally in a longitudinal direction which is toward the cap from the base.

3. A two-piece instrument sterilization container comprising an elongate, hollow base including fluid-impervious surface structure extending between an open end and a closed end in the base to define interior and exterior surfaces of said base, an elongate, hollow cap including fluid-impervious surface structure extending between an open end and a closed end in the cap to define an interior surface of said cap, a plurality of spaced, elongate spines extending along said cap interior surface from said open end, said cap being removably fittable on and with respect to said base along the respective longitudinal axes of the base and cap to define a region of longitudinal surface structure overlap with said spines engaging said exterior surface of said base to form, in the resultant assembly, plural fluid passages through said overlap region.

4. The container of claim 3, wherein said base further includes a ledge formed on said exterior surface of said base surface structure to limit surface structure overlap.

5. A two-piece sterilization container comprising a rigid, elongate, hollow base including generally transparent, fluid-impervious surface structure extending between an open end and a closed end of said base, said base including fitment structure formed on the outside of said base a predetermined distance from said open end, and a rigid, elongate, hollow cap including generally transparent, fluid-impervious surface structure extending between an open end and a closed end of said cap, and said cap including cap fitment structure formed on the inside of said cap adjacent said open end, with said base and cap fitment structures accommodating reversible, direct-contact, combination of said cap and said base along a longitudinal axis to provide a region of longitudinal-surface-structure overlap between said base and cap, said base fitment structure limiting overlap via operative engagement of said base fitment structure with said cap fitment structure, said cap and base forming, when fitted, a non-closable, linear fluid passage in a region of overlap between said base and cap, said passage communicating between the inside and the outside of the container such that fluid flow toward the inside of the container is in a longitudinal direction generally toward the cap from the base.

6. A system for use in sterilizing objects comprising a sterilization device including an elongate inner chamber extending along an insertion axis and dividable into plural modular compartments which also extend along the insertion axis, defining modular boundaries, and a plurality of elongate two-piece containers, each container including a tubular base having an open end and a closed end, and including base fitment structure formed on said base adjacent to the open end, and an elongate tubular cap removably fittable over and with respect to said base having an open end and a closed end, and including cap fitment structure formed on said cap adjacent to the open end, said cap and base fitment structures accommodating reversible, direct-contact, longitudinal-surface-structure fitment overlap, with the cap and base fitted together, defining a longitudinally extending fluid passage between the base and cap structured to allow fluid flow therethrough toward the inside of the container from the outside thereof in a longitudinal direction within said passage generally toward the cap from the base, said cap and base each defining rigid, fluid-impervious surface structure with said cap surface structure defining a cross-sectional cap area greater than a cross-sectional base area defined by said base surface structure, said containers being inserted into said modular compartments of said chamber along the insertion axis with the surface structures of said containers being generally congruent with said modular boundaries of respective modular compartments within said chamber, each container being arranged in opposite longitudinal orientation relative to an adjacent container to accommodate fluid flow into and between containers.

7. The system of claim 6, wherein multiple sterilization containers are arranged inside said sterilization chamber to generally occupy all modular compartments.

8. The container of claim 6, wherein said cross-sectional cap area is generally triangular.

9. The container of claim 6, wherein said cross-sectional base area is generally triangular.

10. The container of claim 6, wherein said base includes base fitment structure and said cap includes cap fitment structure, said base and cap fitment structures being formed on said base and said cap adjacent their respective open ends, accommodating reversible, direct-contact, longitudinal-surface-structure fitment overlap, with the cap and base fitted together, defining plural longitudinally extending fluid passages to the interior of the container, such fluid passages being arranged about the container's perimeter.

* * * * *